(12) United States Patent
Es-Souni

(10) Patent No.: US 8,771,830 B2
(45) Date of Patent: Jul. 8, 2014

(54) HYDROPHOBIC COATING AND PROCESS FOR PRODUCTION THEREOF

(75) Inventor: Mohammed Es-Souni, Mielkendorf (DE)

(73) Assignee: Fachhochschule Kiel, Kiel (DE)

( * ) Notice: Subject to any disclaimer, the term of this patent is extended or adjusted under 35 U.S.C. 154(b) by 574 days.

(21) Appl. No.: 12/995,586

(22) PCT Filed: May 19, 2009

(86) PCT No.: PCT/DE2009/000707
§ 371 (c)(1),
(2), (4) Date: Jan. 20, 2011

(87) PCT Pub. No.: WO2009/146674
PCT Pub. Date: Dec. 10, 2009

(65) Prior Publication Data
US 2011/0111213 A1 May 12, 2011

(30) Foreign Application Priority Data
Jun. 5, 2008 (DE) .......................... 10 2008 026 988

(51) Int. Cl.
*B32B 9/00* (2006.01)
*C09K 3/18* (2006.01)
*A61L 33/02* (2006.01)

(52) U.S. Cl.
USPC .......................................... 428/336; 252/194

(58) Field of Classification Search
CPC ............. B32B 9/00; C09K 3/18; A61L 33/02
USPC ........................................................ 428/336
See application file for complete search history.

(56) References Cited

U.S. PATENT DOCUMENTS

| | | | | |
|---|---|---|---|---|
| 6,013,372 A | * | 1/2000 | Hayakawa et al. | 428/411.1 |
| 2002/0119307 A1 | * | 8/2002 | Boire et al. | 428/336 |
| 2004/0202890 A1 | | 10/2004 | Kutilek et al. | |

FOREIGN PATENT DOCUMENTS

WO  WO 2005/105304  11/2005

OTHER PUBLICATIONS

Murat et al., WO 2005105304(A2), "Use of Photocatalytic TiO2 Layers for Functionalizing Substrates", Nov. 10, 2005 (Machine Translation).*
Es-Souni, M., Fischer-Brandies, H. and Es-Souni, M. (2008), Versatile Nanocomposite Coatings with Tunable Cell Adhesion and Bactericidity. Adv. Funct. Mater., 18: 3179-3188. doi: 10.1002/adfm. 200800354, Sep. 29, 2008.*
Klee et al., "Surface Modification of a New Flexible Polymer with Improved Cell Adhesion", Journal of Materials Science: Materials in Medicine, No. 5, pp. 592-595, 1994.
Yoon et al., "Superhydrophobicity of PHBV Fibrous Surface with Bead-On-String Structure", Journal of Colloid and Interface Science, No. 320, pp. 91-95, 2008.
Xu et al., "Surface Modification of Polyester Fabric by Corona Discharge Irradiation", European Polymer Journal, No. 39, pp. 199-202, 2003.
Liston et al., "Plasma Surface Modification of Polymers for Improved Adhesion: A Critical Review", Journal of Adhesion Science Technology, vol. 7, No. 10, pp. 1091-1127, 1993.
Page et al., "Titania and Silver—Titania Composite Films on Glass—Potent Antimicrobial Coatings", Journal of Materials Chemistry, No. 17, pp. 95-104, 2007.

* cited by examiner

*Primary Examiner* — Callie Shosho
*Assistant Examiner* — Cheng Huang
(74) *Attorney, Agent, or Firm* — Cozen O'Connor

(57) ABSTRACT

Substrate having a silver-ion containing titanium oxide coating having a silver content of greater than or equal to 0.2 of Ag/l of Ti to less than or equal to 0.4 of Ag/l of Ti, wherein the coating is X-ray amorphous and the hydrophobicity of the coating can be reduced persistently by illumination.

4 Claims, 3 Drawing Sheets

US 8,771,830 B2

HYDROPHOBIC COATING AND PROCESS FOR PRODUCTION THEREOF

CROSS-REFERENCE TO RELATED APPLICATIONS

This application represents a National Stage application of PCT/DE2009/000707 entitled "Hydrophobic Coating and Process for Production Thereof" filed May 19, 2009, pending.

BACKGROUND OF THE INVENTION

The invention relates to a silver-ion-containing titanium oxide coating that has an alterable hydrophobicity, and a process for production thereof.

The tendency of a substance to mix with water is described by the hydrophilicity or its counter part, the hydrophoby. The extent of the hydrophoby of a surface is described by the hydrophobicity. A physical measure for the hydrophobicity of a surface is the contact angle, and DIN EN 828 describes how it is measured. At a contact angle of 0°, water forms a monomolecular film on the solid surface, while at a contact angle of 180° a drop of water only touches the solid surface in a point. At a small contact angle close to 0° there is strong interaction between the surface and the drop of water, the surface is termed hydrophilic. At contact angles around 90° and above the surfaces are hydrophobic ones and the wettability is very low here. In the case of even larger contact angles, the surfaces are called superhydrophobic, in the case of contact angles of approximately 160°, the term lotus effect is used.

The flow behavior of a flowing medium is also determined by the hydrophobicity of the surrounding vessel walls.

For a multiplicity of applications, for example medical implants as for example stents, microscale reactors, inside coatings of storage and reaction vessels, a precise and permanent setting of the hydrophoby/hydrophilicity is of great importance even in a very small space.

A hydrophobicity that can be set is of extreme importance, in particular in the area of medical technology, since on the one hand it shall be possible for body fluids to flow past without hindrance and in an optimum manner, on the other hand direct contact to the body tissue is present and it is desired that the implant grows on. Here the demand is therefore for a single implant to have quite different degrees of hydrophobicity. A particular advantage could be if the hydrophobicity can be matched exactly to the patient while inserting the implant. Subsequent structuring of materials/layers that are suitable for this purpose into neighboring hydrophobic/hydrophilic areas for application in microfluidics can further be used.

The choice of suitable carriers for a coating is limited as layers that have been applied must be cured by thermal treatment above 200° C. Not all carriers are suited for these temperatures.

The costs of a manufacturing process depend among others on the required energy and thus on the heating power necessary for carrying out the process, a reduction in the manufacturing temperature below 200° C. saves energy costs.

The publication "Titania and silver-titania composite films on glass-potent antimicrobial coatings" Page et. al.; J. Mater. Chem., 17, 95-104 likewise describes hydrophilic titanium-dioxide layers to which small amounts of silver ions have been added. Before being exposed, the layers have contact angles of 15° and no antimicrobial action; during exposure with UV light, a non-persistent ("persistent" can perhaps be replaced by "permanent") antimicrobial action and a likewise non-persistent contact angle changing in the direction of super-hydrophilicity can be observed. A furnace having temperatures of 500 to 600° C. is used to produce the part-crystalline network.

Treating polymers by plasma, corona discharge and UV radiation for the purpose of manufacturing hydrophilic and hydrophobic surfaces are known from [M. R. Wertheimer, L. Martinu, E. M. Listen, J. Adhes. Sci. Technol., 1993, 7(10), 1091.], [D. Klee, R. V. Villari, H. Hocker, B. Dekker, C. Mittermayer, J. Mat. Sci.: Mat. Med. 1994, 5, 592.], [Y. I. Yoon, H. S. Moon, W. S. Lyoo, T. S. Lee, W. H. Park, J. Colloid Interface Sci. 2008, 320, 91] and [W. Xu, X. Liu, European Polymer J. 2003, 39, 199]. However, no persistent effect can be achieved.

The effect described here cannot be permanently achieved by a one-time irradiation of UV light, i.e. it is not persistent.

It is the object of the invention to provide a process for the production of a coating that can be permanently set to a persistent value in terms of its hydrophobicity by a single subsequent illumination.

It is a further object of the invention to provide a process for the production of a coating that can be permanently set to a persistent value in terms of its hydrophobicity even in the micrometer-scale range by a single subsequent illumination.

It is also the object of the invention to provide a process for the production of a coating that can be permanently set to a persistent value in terms of its hydrophobicity by a single subsequent illumination where temperatures of more than 200° C. are dispensed with.

Over and above this it is an object of the invention to provide a coating that can be set to a persistent value permanently in terms of its hydrophobicity even in the micrometer-scale range by a subsequent, single exposure.

SUMMARY OF THE INVENTION

The invention comprises a production process for a coating consisting of the steps already known for producing a titanium-oxide layer using the sol-gel method:

Production of a solution of a titanium precursor in a suitable solvent
adding an aqueous solution for hydrolyzing the Ti precursor
producing a silver-ion-containing solution in a suitable solvent
adding the silver-ion-containing solution to the Ti-containing solution
applying on a suitable carrier
drying the material
The following process steps are optional:
acidifying the Ti precursor solution
storing the solutions while cooling
filtration The steps "Production of a silver-ion-containing solution in a suitable solvent" and "Drying the material" are varied as follows according to the invention.

Subsequent heating above 200° C. by sintering and/or by pyrolysis is dispensed with. The silver ions are further used in a molar ratio of Ag to Ti of 0.2-0.4 to 1, preferably from 0.25-0.35 to 1, particularly preferable from 0.3 to 1. The material is dried at room temperature in the absence of light.

When these further developments of the process steps are carried out, one arrives for the first time at x-ray amorphous coatings that can be accurately set in terms of their hydrophobicity to a specific value persistently also in the range below 1 μm (as a function of the structuring method, for example using electron-beam lithography, sub-microscopic structure definitions can be achieved), that are likewise a subject-matter of the invention.

BRIEF DESCRIPTION OF THE DRAWINGS

The invention can be explained in more detail using the following figures, in which.

DETAILED DESCRIPTION OF THE INVENTION

The molar ratio of Ag to Ti 0.2-0.4 to 1, preferably from 0.25-0.35 to 1, particularly preferred from 0.3 to 1 provides for the generation of a meta-stable $TiO_2Ag_xO$ solution, this in turn forms the coating without the conventional heating and/or sintering and/or pyrolysis.

Exposing the inventive layer using UV light having a wavelength 250 nm to 400 nm, a contact angle of $30°±5°$ is achieved, that does not change again, even after turning off the UV source and ageing of the material, however, the non-irradiated layer shows a contact angle of $99°±2°$.

For the first time the effect can be observed that the contact angle that has been set by irradiation does not change any more even after removing the irradiation source, that is to say it is persistent.

Figure 1:
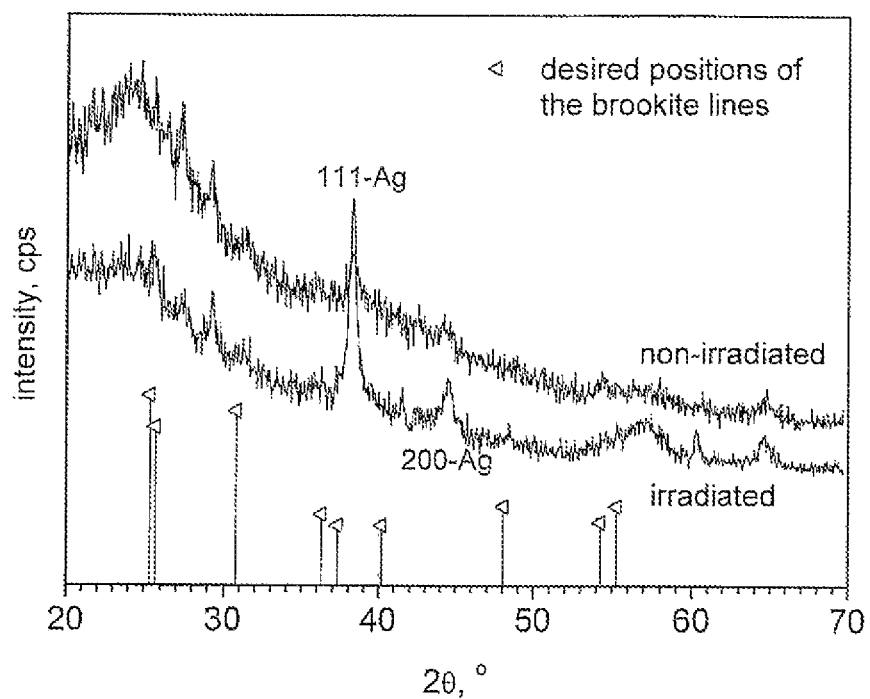
FIG. 1 shows x-ray diffraction patterns of the irradiated (ir) and the non-irradiated layer (nir)

FIG. 1 shows the x-ray diffraction patterns of the irradiated (ir) and the non-irradiated layer (nir). The crystal reflexes of the titanium-dioxide modification brookite (PDF 29-1360) have also been included in the drawing.

The non-irradiated and also the irradiated layers show no crystal reflexes of the titanium dioxide or the silver oxide, the sample is x-ray amorphous, after the irradiation only the presence of silver is indicated in the absence of a titanium-dioxide or silver-oxide crystal network.

Figure 2:
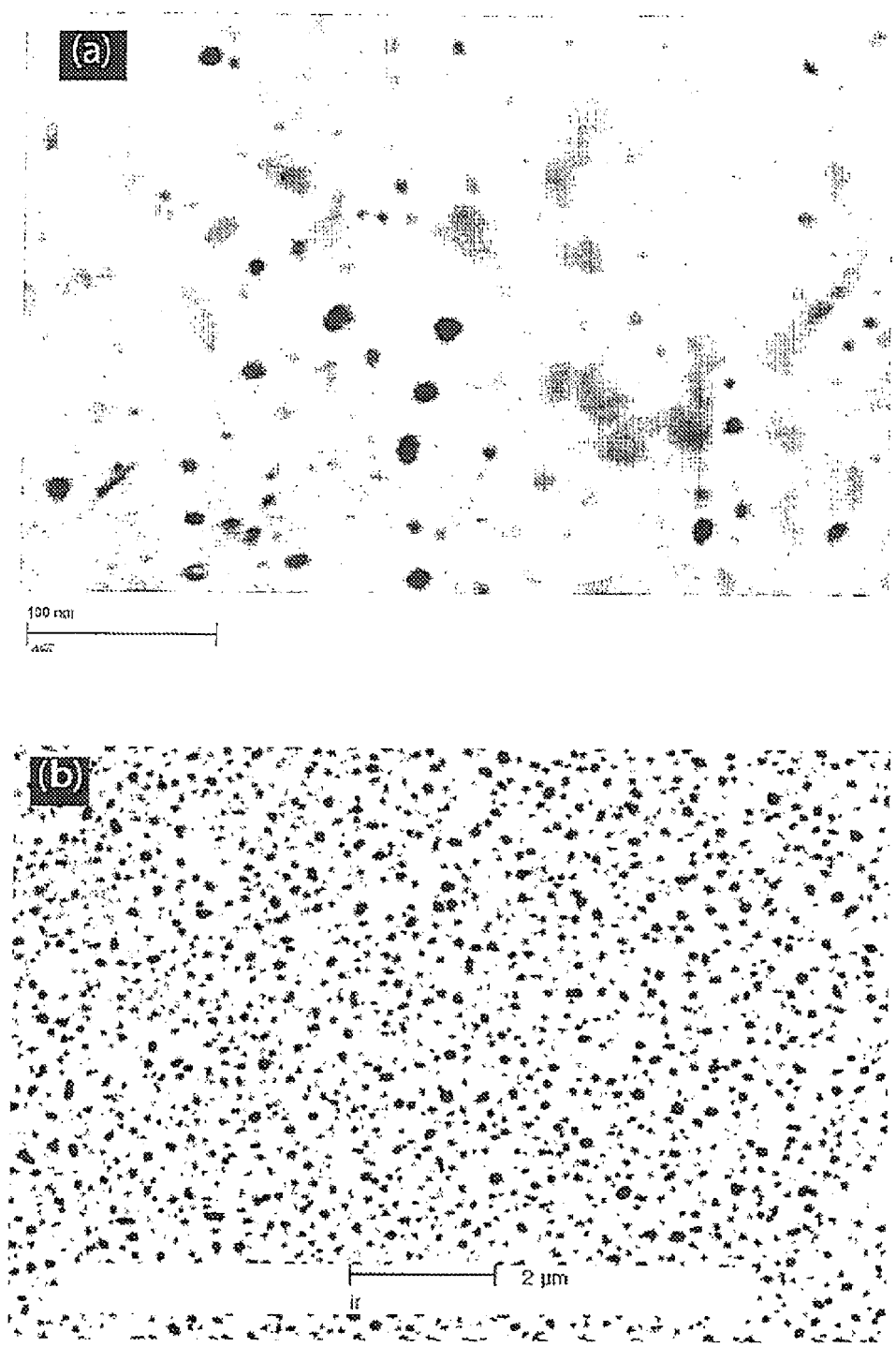
FIG. 2 shows electron microscope images of the non-radiated layer (a) (FE-REM) and the irradiated (b) layer (REM), that were inverted for reasons of better presentation, that is, changed to be a negative.

FIG. 2 shows the electron-microscope images (REM) of the non-illuminated layer (c) and the illuminated (d). The non-illuminated layer only shows structures that are markedly smaller than 100 nm, while the exposure leads to structures in the order of magnitude of about 100 nm.

The non-existence of crystal structures and structures having a size greater than 100 nm and the homogeneity, that is thus present, of the non-illuminated hydrophobic layer enables the hydrophobicity to be set by exposing the material with an accuracy of the limit of 1 μM if exposure masks are applied that are correspondingly sharp and can be placed well. The limiting factor is here no longer the coating but the inaccuracy resulting from the wavelength of the exposure light and from the placement and constitution of the exposure mask.

Figure 3:
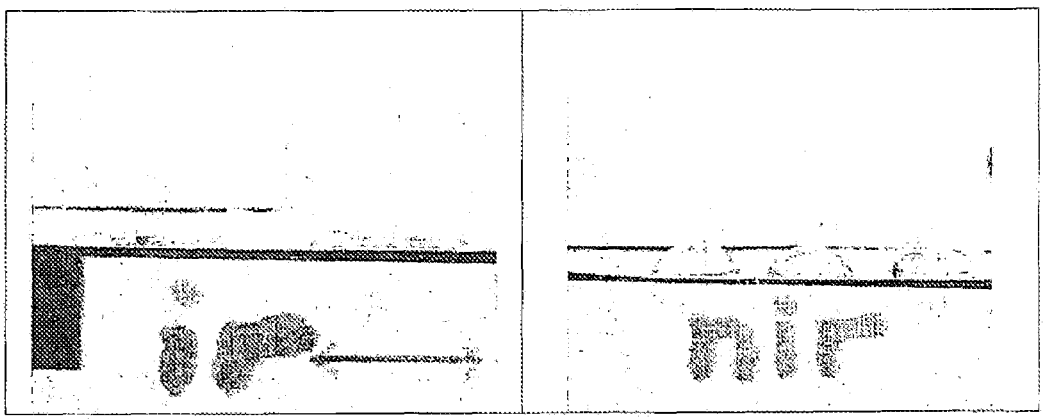
FIG. 3 shows wetting experiments: (a) irradiated (ir); (b) non-irradiated (nir) layer.
Figure 4:
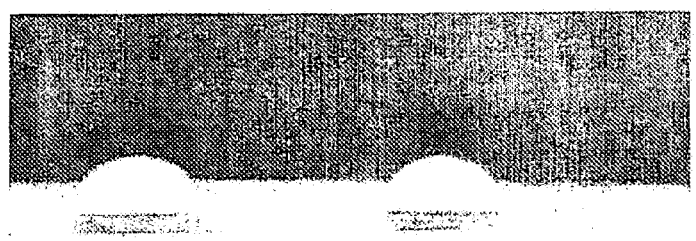
FIG. 4 shows the wetting of a Teflon film in comparison.

FIG. 3 illustrates the wettability of an illuminated layer (ir) and a non-illuminated layer (nir) using a drop of water. FIG. 4 shows a drop of water in comparison on a Teflon layer.

DEFINITIONS

Titanium-Precursor:
Alkoxides of titanium, preferably $C_{1-12}$ alkoxides like for example tetraisopropyl orthotitanate or tetrabutyl orthotitanate, can be used as Ti precursor.

Solvents:
Examples for suitable solvents are aliphatic alcohols, ethers, aldehydes, ketones, water, ester, alkyl halogenides, aromatic hydrocarbons, sulfoxides, sulfones, amides or their mixtures.

Application on the Layer:
Application on the carrier material can take place by usual wet-chemical coating processes. Examples are dipping methods, electro-dipping methods, spin-coating, spraying, sputtering, spinning, drawing, centrifuging, casting, rolling, painting, film-casting, flooding, slot coating, spin coating, meniscus coating, curtain coating, roller coating or other printing methods.

Irradiation for Setting the Hydrophobicity:
Irradiation using electromagnetic light can take place at a wavelength of 250 nm to 800 nm, irradiation at 250 nm to 400 nm is preferable. Typical irradiation times amount to approximately 20 minutes.

The Thickness of the Coating:
The thickness of the coating should be at least 50 nm, 300 nm to 500 nm being particularly preferable.

Material and Methods
To produce the coating, a $TiO_2$ Ag solution is prepared at first, that can then be applied to any substrates by dipping, spraying or spin-coating.

The preparation of a $TiO_2$ Ag solution having a molar ratio of Ti—Ag of 1:0.3 is shown as an example below.

The weighed portion and the molar ratios are listed in the table below:

| substance | mw | mol | G | ml | molar ratio |
|---|---|---|---|---|---|
| Ti isopropoxide | 987.9 | 0.004 | 1.136 | 1.18 | 1.00 |
| AgNO$_3$ | 169.9 | 0.001 | 0.216 | — | 0.30 |
| EtOH (>99.9%) undenatured | 46.07 | 0.306 | 18.400 | 23.29 | 76.77 |
| H$_2$O | 18 | 0.016 | 0.280 | 0.29 | 4.00 |
| HNO$_3$ (65%) | 63.01 | $2.9 \times 10^{-4}$ | 0.028 | 0.02 | 0.072 |

Preparation takes place at room temperature.

1.18 ml tetraisopropyl orthotitanate are added to 6 ml ethanol and the mixture is stirred for 10 minutes (→solution 1). In a further vessel, 0.29 ml of water and 6 ml of ethanol are mixed and likewise stirred for 10 minutes (→solution 2). Then the aqueous ethanol solution (solution 2) is added to the ethanolic tetraisopropyl ortho-titanate solution (solution 1) and the solution is stirred for a further 30 minutes (→solution 3). In a further vessel 0.02 ml of nitric acid (65%) are added to 6 ml of ethanol and stirred for 10 minutes (→solution 4). The ethanolic nitric-acid solution (solution 4) is added drop by drop to the Ti solution (solution 3) while stirring, after that stirring continues for another 30 minutes (→solution 5). 0.216 g of silver nitrate are dissolved in 5.29 ml of water while stirring and using ultrasound (→solution 6). The silver-nitrate solution (solution 6) is added to the Ti solution (solution 5) and stirred for another 60 minutes.

Before the finished solution is applied to the substrate, filtering takes place by means of a 0.2 μm filter. The solution can be stored at −40° C. Before the stored vessel is opened, the solution should first be brought to room temperature to reduce the condensation of atmospheric moisture.

Irradiation Using UV Light:

Irradiation of the inventive layers takes place for 20 minutes in a closed chamber having a 150 W UV lamp (Supratec UV-High pressure lamp, Radium; 250 nm<λ<400 nm).

Measurement of the Contact Angle:

Measurement takes place using a video-based measuring device Crüss-G10, Hamburg.

X-Ray Diffractometry

The powder diffraction patterns (XRD) were taken at a grazing angle (GI) using a Seifert 3000 PTS 4-circle-diffractometer, with the Cu Kα line (λ=1.5418 Å). The GI angle was 5°.

Electron Microscopy:

The SEM images were taken using Philips XL 30, equipped with energy-dispersive x-ray spectroscopy (EDS, EDAX CDU Leap Detector), the FE-SEM using a Schottky emitter (FE-SEM, Zeiss Ultraplus, Germany).

The invention claimed is:

1. A substrate comprising a silver-ion-containing titanium oxide coating having a silver content in a molar ratio of greater than or equal to 0.2 of Ag/l of Ti to less than or equal to 0.4 of Ag/l of Ti, wherein the silver-ion-containing titanium oxide coating is completely X-ray amorphous and composed so that the hydrophobicity of the silver-ion-containing titanium oxide coating is persistently reduced by illumination.

2. The substrate according to claim 1, characterized in that the hydrophobicity of the coating can be reduced persistently by illumination using a wavelength of 250 nm to 400 nm.

3. The substrate according to claim 1, characterized in that the coating was cured at a temperature equal or less than 200° C.

4. The substrate according to claim 1, characterized in that the coating has a thickness of 300 to 500 nm.

* * * * *